(12) United States Patent
Kluge

(10) Patent No.: US 6,830,019 B2
(45) Date of Patent: Dec. 14, 2004

(54) VALVE ACTUATION IN COMBUSTION ENGINES WITH ARTIFICIAL MUSCLES

(75) Inventor: Torsten Kluge, Overath (DE)

(73) Assignee: Ford Global Technologies, LLC, Dearborn, MI (US)

( * ) Notice: Subject to any disclaimer, the term of this patent is extended or adjusted under 35 U.S.C. 154(b) by 0 days.

(21) Appl. No.: 10/687,346

(22) Filed: Oct. 16, 2003

(65) Prior Publication Data

US 2004/0118366 A1 Jun. 24, 2004

(30) Foreign Application Priority Data

Oct. 17, 2002 (EP) ............................................ 02102458

(51) Int. Cl.$^7$ ................................................. F01L 9/04
(52) U.S. Cl. ...................................... 123/90.11; 92/92
(58) Field of Search ........................... 92/92; 123/90.11

(56) References Cited

U.S. PATENT DOCUMENTS

| | | | |
|---|---|---|---|
| 6,109,852 A | | 8/2000 | Shahinpoor et al. |
| 6,310,583 B1 | * | 10/2001 | Saunders .................... 343/786 |
| 6,349,685 B1 | | 2/2002 | Kolmanovsky et al. |
| 6,628,040 B2 | * | 9/2003 | Pelrine et al. .............. 310/307 |
| 6,730,123 B1 | * | 5/2004 | Klopotek ................... 623/6.22 |
| 2002/0026794 A1 | | 3/2002 | Shahinpoor et al. |

FOREIGN PATENT DOCUMENTS

EP          0924033          6/1999

OTHER PUBLICATIONS

The Sound of Muscle, Information Acess Company, Business News Publishing Co., No. 4, vol. 48, p. 8; ISSN: 0003–679X; Apr. 1, 2000.*
"Microactuators toward microvalves for responsive controlled drug delivery"; Lei–Mei Low et al., Sensors and Actuators B 67 (2000), pp. 149–160.
"Carbon Nanotube Actuators", Ray H. Baughman et al.; May 21, 1999; vol. 284, Science; pp. 1340–1344.

* cited by examiner

Primary Examiner—Thomas Denion
Assistant Examiner—Zelalem Eshete
(74) Attorney, Agent, or Firm—Diana D. Brehob

(57) ABSTRACT

The invention relates to a valve device for controlling the valve tappet of an internal combustion engine of a motor vehicle. In this case, the movement of the valve tappet is generated by contraction/expansion or flexion or stretching of at least one artificial muscle. Furthermore, the artificial muscle can form a gas pressure chamber, by the action of pressure upon which a counterforce can be exerted on the valve tappet. Alternative embodiments of the invention relate particularly to the movement of valve flaps by artificial muscles and to the closing of a valve orifice by an artificial muscle of variable form.

18 Claims, 3 Drawing Sheets

VALVE ACTUATION IN COMBUSTION ENGINES WITH ARTIFICIAL MUSCLES

FIELD OF THE INVENTION

The invention relates to a valve device with a movable valve element, in particular for controlling the gas flow in an internal combustion engine.

BACKGROUND OF THE INVENTION

Valve devices are required in various sectors of industry for controlling flow of a gaseous or liquid medium. Valve devices used in internal combustion engines of motor vehicles are considered below, but without the invention being restricted to them.

Valve devices of internal combustion engines serve for controlling the inlet of combustion air or outlet of the exhaust gases. Typically, a movable valve element in the form of a valve tappet is moved back and forth linearly between an open position and a closed position. According to the prior art, the force necessary for executing this movement may be generated, for example, by camshafts or by means of electromagnetic coils or hydraulic or pneumatic actuators. When known actuators are used, however, there is still a need for improvement with regard to compactness and efficiency.

SUMMARY OF THE INVENTION

An important aim of this improvement is that, when ideal valves are used, the performance of an internal combustion engine can be regulated, without a throttle valve being employed, solely by the time control or timing of the valve opening and by the valve stroke.

Against this background, an advantage of the present invention is that it provides a valve device which is suitable for use in internal combustion engines allowing efficient and flexible valve control.

The valve device according to the invention with a movable valve element has at least one artificial muscle element coupled to the valve element. In this context, the term "coupling" may also mean a physical identity of valve element and muscle element.

Artificial elements are novel actuators which in their properties are similar to or simulate natural musculature. A particular characteristic of artificial muscles is force generation taking place in the volume as a result of atomic or molecular interactions. Often, in a similar way to natural muscles, artificial muscles consist of soft material of variable form. Force generation in known artificial muscles may be based, for example, on electrostatic forces of attraction, on the piezo-electric effect, on ultrasound generation, on a form memory of materials, on ion exchange, on an extension of carbon nanotubes and/or on the incorporation of hydrogen into metal hydrides. Depending on the active principle, artificial muscles may be produced from polymers, in particular polymer gels, from ferroelectric substances, from silicon, from alloys with a form memory or the like. A detailed description of various types of artificial muscles is found, for example, in EP 0 924 033 A2, US 2002/0026794 A1, and U.S. Pat. No. 6,109,852.

Preferably, the valve device described makes use of artificial muscle elements of this type which can be controlled by means of an electrical signal. In particular, the mechanical energy generated by the muscle element can originate from the electrical energy of the signal. Electrically-controlled artificial muscle elements have the advantage that they are compatible with the conventional control technology of an internal combustion engine.

In one embodiment of a valve device, artificial muscle elements are used which can actively contract, actively expand and/or actively change their form, such as, for example, their curvature. Artificial muscle elements which can actively generate a force in two opposite directions can in this case even individually induce the entire movement of the valve element. By contrast, when an artificial muscle element can generate an active force in only one direction, it has to be supplemented by a force generator which is active in the opposite direction, for example a further artificial muscle elements, to make the valve element controllable in the opening and closing directions.

As already explained, in principle, all types of artificial muscle elements can be used for the proposed valve device. In one embodiment, artificial muscle elements based on the interaction of carbon nanotubes are used. Artificial muscle elements of this type are distinguished by a high heat resistance of up to 1000° C. Furthermore, muscle elements of this type can be controlled and expanded by electrical energy (cf. Science of May 21, 1999). A further preferred type of artificial muscle is based on polymer gels (cf. Low, L. W.; Madou, M. J. "Microactuators towards microvalves for controlled drug delivery", Sensors and Actuators B: Chemical, 67 (1–2) (2000) pp. 149–160).

There are numerous possibilities for the structural configuration of the valve element. So that the changes to existing engines are minimal, many known structural elements are adopted. In particular, the valve element may be formed by a valve tappet which is mounted with displacement movability and to which the artificial muscle element is coupled directly or indirectly, that is to say via intermediate components, such as, for example, rocker or drag levers.

According to a special embodiment of the abovementioned valve device with a valve tappet, the latter is coupled to a prestressing element, for example to a helical spring. The prestressing element can generate a force in one direction of movement of the valve tappet. The artificial muscle element then only has to be capable of generating a force in the opposite direction to make the valve element as a whole controllable.

In another embodiment of the valve device with a valve tappet, the latter is coupled to a gas pressure chamber in such a way that a pressure rise in the gas pressure chamber causes a movement of the valve tappet. By the pressure in the gas pressure chamber, therefore, a force can actively be exerted on the valve tappet.

Preferably, in the last-mentioned embodiment with a gas pressure chamber, the walls of the gas pressure chamber are formed completely or at least partially by the artificial muscle element. This double function of the artificial muscle element contributes to a more compact construction which saves material and allows direct interaction between the artificial muscle element and the pressure in the gas pressure chamber.

In another development of the valve device, the valve element is formed by a pivotally movable flap which, depending on the set angle, can open or close a throughflow orifice. In particular, in this case, a plurality of such flaps may also interact jointly to control the throughflow orifice. A valve element of this type with a plurality of flaps is more robust against total failure and can be actuated more quickly, since a plurality of flaps simultaneously execute a travel into the opening or closing position.

Furthermore, it is possible to have embodiments of the valve device in which the valve element is formed by the artificial muscle element itself, that is to say is physically identical to it. In this case, the artificial muscle element may be arranged, for example, in a passage and close or open the latter as a result of an active change in form or in volume.

The above advantages and other advantages, objects, and features of the present invention will be readily apparent from the following detailed description of the preferred embodiments when taken in connection with the accompanying drawings.

BRIEF DESCRIPTION OF DRAWINGS

The invention is explained in more detail below by way of example with the aid of the Figures with which.

DETAILED DESCRIPTION

Figure 1:
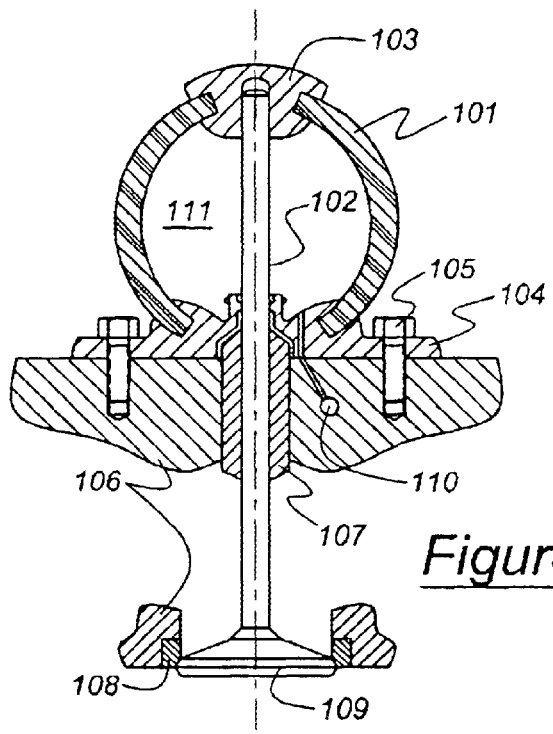
FIG. 1 shows a section through a first embodiment of a valve device according to the invention, in which artificial muscles act in opposition against a gas pressure.

FIG. 1 shows a sectional illustration of a first embodiment of a valve device according to the invention, which can be used, in particular, as an inlet or outlet valve on the cylinder head 106 of an internal combustion engine. According to the form of construction of such valve devices, which is known per se, this has a valve tappet 102 which is movable in displacement linearly (up and down) and at the lower end of which a valve disk 109 is arranged. The valve disk 109 cooperates with a valve seat 108 formed in the cylinder head 106, to selectively open or close an orifice for gas flow. A valve guide 107 is provided in the passage of the valve tappet 102 through the cylinder head 106 for sealing off the valve element relative to the outside and for guiding the latter with as little friction as possible.

What is novel in the valve element illustrated in FIG. 1 is the actuator for generating an active force on the valve tappet 102. This actuator is formed by artificial muscle elements 101 which are fastened to a baseplate 104 fastened on the cylinder head 106 by means of a screw 105 and to a headplate 103. Furthermore, the upper end of the valve tappet 102 is seated in the headplate 103 which, like the baseplate 104, typically is comprised of metal.

The artificial muscle elements 101 may be based on carbon nanotubes, which are particularly heat-resistant and which, controlled by electrical signals, can expand (cf. Science of May 21, 1999). However, it is likewise also possible to employ artificial muscles based on polymer hydrogels, which, controlled by electrical signals, can contract, or artificial muscles which allow both active contraction and expansion. Moreover, artificial muscles with a low ratio of expansion to contraction (for example carbon nanotubes) are suitable, which are bundled in paper-like multilayer structures and allow a considerable curvature of the entire muscle structure.

A downwardly directed movement of the valve tappet 102 and consequently an opening of the valve can be brought about by means of an active contraction or flexion of the artificial muscle elements 101. If the artificial muscle elements 101 can actively expand or stretch, they can also bring about the opposite closing movement of the valve tappet 102.

Additionally or alternatively, a closing movement of the valve tappet 102 can be brought about with the aid of a gas pressure chamber 111 which surrounds the upper end of the valve tappet 102, said end being located outside the cylinder head 106, and which is delimited by the artificial muscle elements 101, the headplate 103 and the baseplate 104. If said elements form a closed envelope and the artificial muscles 101 are designed to be gastight, for example by means of a corresponding coating, a higher pressure can selectively be generated in the gas pressure chamber 111 and leads to an upward movement of the valve tappet 102 into the closing position. This action of the gas pressure chamber may, if appropriate, be combined with an active expansion of the artificial muscle elements 101, if the latter are capable of this. For generating a higher pressure in the gas pressure chamber 111 or for a pressure reduction, the gas pressure chamber 111 is connected to a regulated gas pressure source (not illustrated) via a duct 110.

Figure 2:
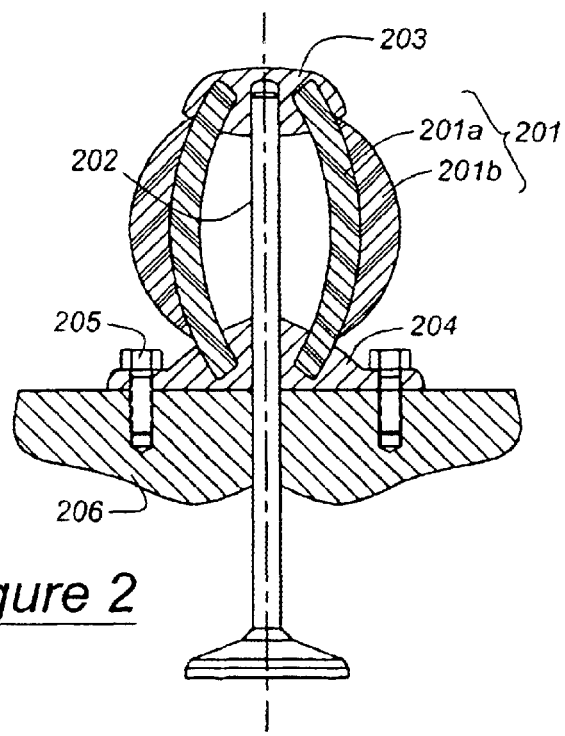
FIG. 2 shows a section through a second embodiment of a valve device according to the invention, in which artificial muscles act in opposition against each other.

FIG. 2 shows a modified embodiment of a valve device, parts similar or identical to those in FIG. 1 being provided here and in the remaining Figures with reference symbols of which the last two digits are identical.

The valve device of FIG. 2 consists of a valve tappet 202, movable up and down, which is led through a cylinder 206 and is fastened at its upper end in a headplate 203. Furthermore, first artificial muscle elements 201a acting as antagonists are fastened to the headplate 203 and to a baseplate 204 which is screwed to the cylinder head 206.

A counterforce to the antagonists 201a is generated by artificial muscle elements 201b which act as protagonists and which are likewise fastened to the headplate 203 and to the baseplate 204. In contrast to the antagonists 201a, the protagonists 201b can execute active expansion or stretching and thereby generate an upwardly directed force on the valve tappet 202. If the wall formed by the antagonists 201a and the protagonists 201b is gastight, it can act as a gas pressure chamber in the same way as in FIG. 1. Moreover, the activation and deactivation of the antagonists 201a and protagonists 201b can in each case take place reciprocally.

Figure 3:
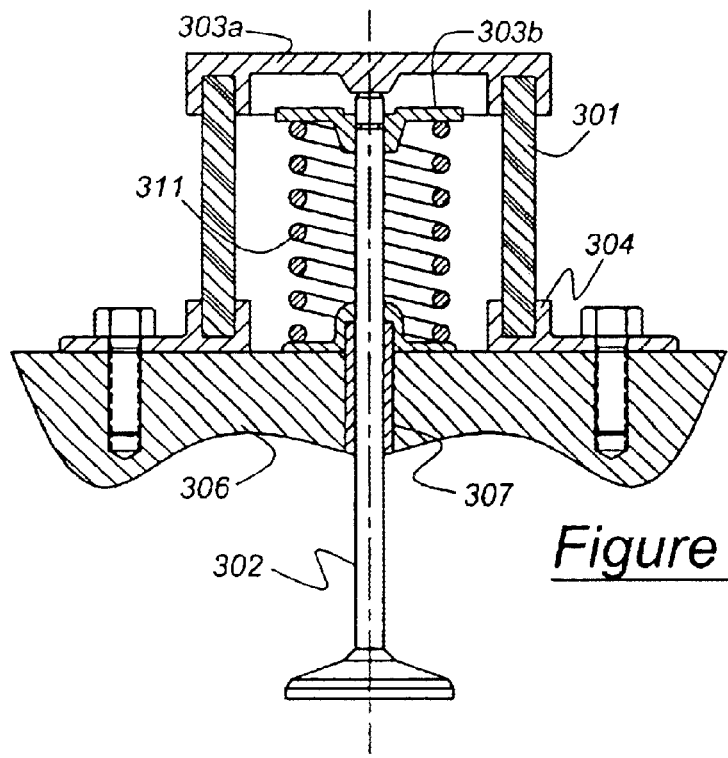
FIG. 3 shows a section through a third embodiment of a valve device according to the invention, in which artificial muscles and a helical spring act indirectly on the upper end of a valve tappet.

FIG. 3 shows a valve device, in which the valve tappet 302 led through the cylinder head 306 carries at its upper end a valve spring plate 303b. Between the valve spring plate and the cylinder head 306 is supported a valve spring 311 which exerts an upwardly directly prestress on the valve tappet 302 and therefore urges the latter into the closing position. So that the valve tappet 302 can be moved downward into an open position, artificial muscle elements 301 are provided, which extend between a headplate 303a and a baseplate 304 firmly screwed to the cylinder head 306 and which can actively contract and/or curve. Since the headplate 303a is supported on the upper end of the valve tappet 302, the latter is pressed downward in the event of a contraction of the artificial muscles 301. Furthermore, in this arrangement, the artificial muscles 301 prevent the headplate 303a from being lost.

An arrangement of this type has the advantage that the helical spring 311 applies a restoring force, so that artificial muscles 301 which can generate a force in only one direction can be used. Furthermore, many features of conventional valve devices can be retained.

Figure 4:
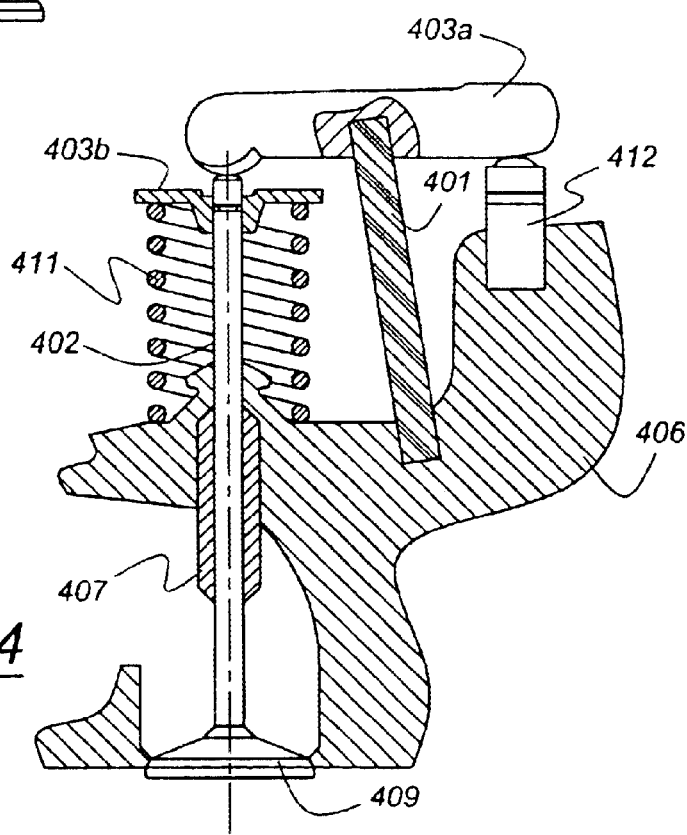
FIG. 4 shows a section through a fourth embodiment of a valve device according to the invention, in which artificial muscles act on drag levers.

The latter also applies to the valve device shown in FIG. 4, in which the valve tappet 402 can be pressed downward into an open position via a pivotally movably mounted rocker lever 403a. The restoring force urging into the closing position is applied, in a similar way to FIG. 3, by helical spring 411 which is supported between the cylinder head 406 and the valve spring plate 403b.

The artificial muscle element 401 is arranged between the cylinder head 406 and the rocker lever 403a in the same way as illustrated in FIG. 4 or in an equivalent way. As a result of contraction and/or flexion, said artificial muscle element can exert on the rocker lever 403a a downwardly directed force which pulls the latter downward and thereby transfers the valve 402 indirectly into an open position. Furthermore, the artificial muscle 401 prevents the rocker lever 403a from being lost.

Figure 5:
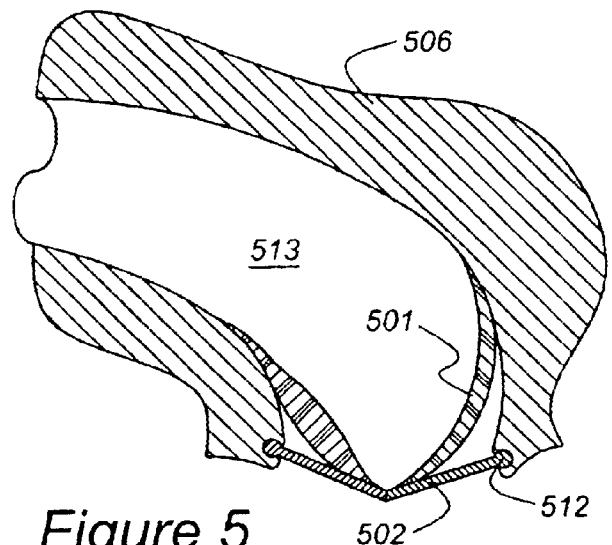
FIG. 5 shows a section through a fifth embodiment of a valve device according to the invention, in which pivotally movable flaps are controlled by artificial muscles.
Figure 6:
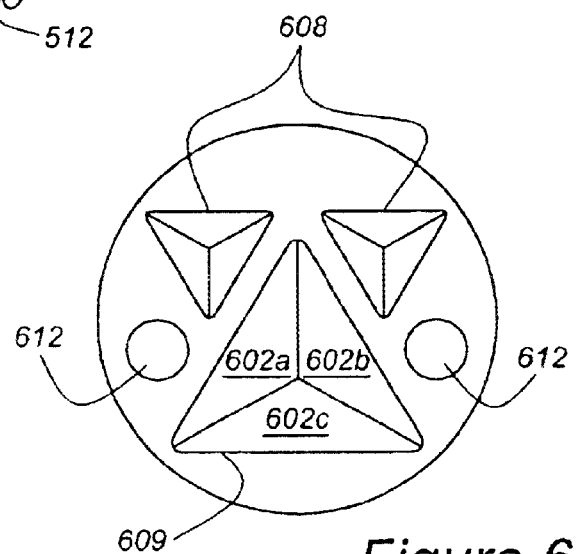
FIG. 6 shows the arrangement of flap valves according to FIG. 5 in the head of an engine cylinder.

FIGS. 5 and 6 show a valve device which differs to a greater extent from known design principles. In this case, the valve elements provided are flaps 502 which are mounted pivotally movably at the end of a gas duct 513 in gastight hinge joints 512. Fastened to each of the flaps 502 is in each case at least one artificial muscle element 501 which is attached with its other end to the cylinder head 506. As a result of a contraction/expansion or flexion/stretching of the artificial muscle elements 501, the valve flaps 502 can be pivoted and therefore transferred out of the closing position shown in FIG. 5 into an open position.

FIG. 6 shows a cylinder head from below. In this case, two triangular outlet orifices 608 and one large triangular inlet orifice 609 can be seen next to the two spark plugs 612. Said orifices are controlled in each case by means of three triangular valve flaps 602a, 602b, 602c which, in FIG. 6, are illustrated in the closed state in which they bear sealingly on one another. If necessary, for example in the case of valve orifices with only one flap, the flaps could also bear sealingly on the edge of the valve orifice.

Figure 7:
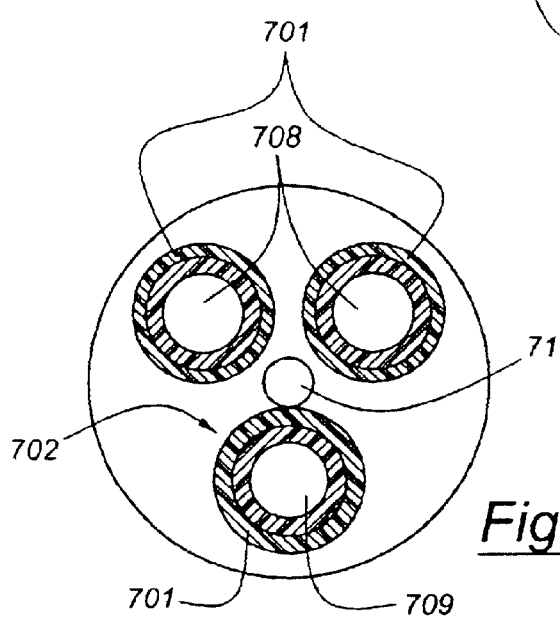
FIG. 7 shows the arrangement of annularly closing artificial muscle elements in the head of an engine cylinder.

FIG. 7 illustrates a further embodiment of a valve device in a view as in FIG. 6, that is to say of the cylinder head from below. A centrally arranged spark plug 712 and also two inlet orifices 708 and one outlet orifice 709 can be seen. Artificial muscle elements 701 are arranged annularly at the edge of said orifices. Each of the artificial muscles 701 is designed as a flat spiral which forms a gastight layered structure. If necessary, gastightness may be ensured by means of a surface coating. FIG. 7 illustrates the artificial muscles 701 in a retracted opening position, in which they open a passage through the valve orifices. In the event of appropriate activation, the artificial muscles 701 can contract completely and thereby close the associated valve orifice.

The valve devices illustrated in the Figures allow a flexible control of a valve and, for example, delayed valve opening or a reduced valve stroke. Furthermore, the valve elements 102, 202, 302, 402, 502, 602, 702 can selectively also be held in any intermediate position within their working range.

While several preferred modes for carrying out the invention have been described in detail, those familiar with the art to which this invention relates will recognize alternative designs and embodiments for practicing the invention. The above-described embodiment is intended to be illustrative of the invention, which may be modified within the scope of the following claims.

We claim:

1. An internal combustion engine valve system, comprising:
   a cylinder head;
   a valve guide mounted in said cylinder head, said valve guide having an aperture; and
   a movable valve element (102, 202, 302, 402, 502, 602, 702) fitted in said valve guide aperture, said movable valve element further comprising at least one artificial muscle element (101, 201, 301, 401, 501, 601, 701) coupled to the valve element (102, 202, 802, 402, 502, 602, 702).

2. The valve device of claim 1, wherein said artificial muscle element (101, 201, 801, 401, 501, 601, 701) is capable of being controlled by an electrical signal.

3. The valve device of claim 1 wherein said artificial muscle element (101, 201, 301, 401, 501, 601, 701) is capable of contracting and expanding.

4. The valve device of claim 1 wherein said artificial muscle element (101, 201, 301, 401, 501, 601, 701) contains polymer gels as active elements.

5. The valve device of claim 1 wherein said artificial muscle element (101, 201, 301, 401, 501, 601, 701) contains carbon nanotubes as active elements.

6. The valve device of claim 1 wherein said valve element is a valve tappet (102, 202, 302, 402) of the internal combustion engine system and said valve tappet is mounted with displacement movability and said artificial muscle element (101, 201, 301, 40) is coupled directly to said valve tappet.

7. The valve device of claim 1 wherein said valve element is a valve tappet (102, 202, 302, 402) of the internal combustion engine system and said valve tappet is mounted with displacement movability and said artificial muscle element (101–401) is coupled indirectly to said valve tappet.

8. The valve device of claim 7, wherein the valve tappet (302, 402) is coupled to a prestressing element (311, 411) which generates a force in one direction of movement of the valve tappet.

9. The valve device of claim 7, wherein the valve tappet (102) is coupled to a gas pressure chamber (111) such that the action of pressure upon the gas pressure chamber causes a movement of the valve tappet.

10. The valve device of claim 7, wherein the walls of the gas pressure chamber (111) are formed completely or partially by the artificial muscle element (101).

11. The valve device of claim 1, wherein the valve element is designed as a pivotally movably mounted flap (502, 602).

12. The valve device of claim 1, wherein the valve element (702) is comprised of the artificial muscle element (701).

13. A method to actuate a valve, comprising:
   providing an electrical signal to said valve, said valve having a movable valve element comprising at least one artificial muscle element coupled thereto wherein said valve is disposed in a cylinder head of an internal combustion engine.

14. The method of claim 13 wherein said cylinder has a valve guide mounted therein, said valve guide having an aperture through which said valve element is mounted.

15. The method of claim 13 wherein said valve element translates in response to said electrical signal.

16. The method of claim 13 wherein said artificial muscle element is capable of contracting and expanding.

17. The method of claim 13 wherein said artificial muscle element comprises polymer gels as active elements.

18. The method of claim 13 wherein said artificial muscle element comprises carbon nanotubes as active elements.

* * * * *